United States Patent [19]
Bobb et al.

[11] Patent Number: 5,172,927
[45] Date of Patent: Dec. 22, 1992

[54] IV STAND COUPLING DEVICE

[75] Inventors: James R. Bobb, Timonium; James J. Zaloudek, Glenn Burnie, both of Md.

[73] Assignee: Church Home and Hospital of the City of Baltimore, Baltimore, Md.

[21] Appl. No.: 765,676

[22] Filed: Sep. 26, 1991

Related U.S. Application Data

[63] Continuation of Ser. No. 629,614, Dec. 18, 1990, Pat. No. 5,083,807.

[51] Int. Cl.⁵ .................................................. A47C 7/62
[52] U.S. Cl. ............................. 280/304.1; 248/231.3; 248/231.5
[58] Field of Search .............. 280/304.1, 250.1, 292, 280/204, 202, 32.7, 411.1, 489, 491.5, 495; 5/507, 508, 503, 118, 119; 248/229, 231.5, 231.6; 297/188, 138, 148, DIG. 4, 172; 296/620; 269/231, 322

[56] References Cited

U.S. PATENT DOCUMENTS

| | | | |
|---|---|---|---|
| 526,798 | 10/1894 | Wise | 248/229 |
| 3,575,250 | 4/1971 | Dykes | 180/11 |
| 3,999,778 | 12/1976 | Markiel | 280/304.1 |
| 4,158,428 | 6/1979 | Bates | 297/DIG. 4 |
| 4,190,280 | 2/1980 | Donohoe | 296/20 |
| 4,305,601 | 12/1981 | Berge | 280/304.1 |
| 4,306,733 | 12/1981 | Cox | 280/204 |
| 4,600,209 | 7/1986 | Kerr, Jr. | 280/400 |
| 4,695,071 | 9/1987 | Johnston | 280/402 |
| 4,702,447 | 10/1987 | Westwood, III | 248/231.5 |
| 4,729,576 | 3/1988 | Roach | 280/493 |
| 4,771,840 | 9/1988 | Keller | 180/11 |
| 4,905,376 | 3/1990 | Neeley | 33/264 |
| 5,009,442 | 4/1991 | Schneider | 280/304.1 |

FOREIGN PATENT DOCUMENTS 0080718 3/1956 Denmark .......................... 280/304.1

Primary Examiner—Margaret A. Focarino
Assistant Examiner—A. M. Boehler
Attorney, Agent, or Firm—Sterne, Kessler, Goldstein & Fox

[57] ABSTRACT

A coupling system and device are disclosed for coupling a wheel chair or other transport device to a wheeled IV stand. In one embodiment, the system comprises a wheel chair having a first footrest and a second footrest, a wheeled IV stand having a pole, and a coupling device for connecting the IV stand to the first and second foot rest of the wheel chair.

2 Claims, 3 Drawing Sheets

TV STAND COUPLING DEVICE

This application is a continuation of application Ser. No. 07/629,614, filed Dec. 18, 1990, now U.S. Pat. No. 5,083,807.

BACKGROUND OF THE INVENTION

1. Field of the Invention

The present invention relates generally to a device and/or system for connecting one movable object with a second movable object. More specifically, the present invention relates to a coupling device and/or system for connecting a wheelchair or other transport device with a wheeled IV stand.

2. Related Art

Conventional systems and/or devices disclose a wheeled IV stand connected to a transport device. One such system and/or device is disclosed in U.S. Pat. No. 4,511,157 to Wilt et al. (the Wilt patent). The Wilt patent appears to disclose an IV stand that is rigidly connected to the upper frame of a wheel chair. The IV stand is positioned in front of the wheel chair so that the IV stand will be pushed when the wheel chair is pushed. The Wilt patent appears to teach that use of a rigid connection between the IV stand and the wheel chair allows the wheels of the IV stand to be raised off the ground simultaneously with the lifting of the front wheels of the wheel chair. This feature allows the wheel chair and/or IV stand to pass over obstructions on the floor.

Coupling systems and/or devices of the type disclosed by the Wilt patent, however, have several significant disadvantages. One such disadvantage is that such conventional coupling systems and/or devices require, to some extent, modifications to the wheel chair. This is a significant problem in that every wheel chair in a hospital, for example, must be modified before attachment with the IV stand.

Another disadvantage is that conventional coupling systems and/or devices cannot easily fit to all sizes and configurations of wheel chairs. Wheel chair, although conventional in design, vary in size. This is inevitable in that there are many wheel chair manufacturers. Therefore, to be most practical, a coupling device and/or system should be capable of attaching to a variety of wheel chair sizes.

Another disadvantage is that to get over obstructions on a floor, devices exemplified by the Wilt Patent require the lifting or tilting back of the wheel chair. This is a burdensome task, especially when a the IV stand may have a heavy pump of other type of equipment on it. Furthermore, the wheelchair/IV stand combination typically encounters ramps (upward and downward sloping). The rigid connection exemplified by the Wilt device may not allow the wheel chair/IV stand combination to travel over ramps without the tilting back of the wheel chair.

OBJECTS OF INVENTION

One object of the present invention is to provide a coupling device that can couple (attach) a conventional wheeled IV stand to a conventional wheel chair without any modifications to the wheel chair or the IV stand.

Another object of the present invention is to provide a coupling device that can quickly connect and disconnect to the wheel chair.

Yet another object of the present invention is to provide a coupling device that can be easily adjusted so that it may attach to wheel chairs of different sizes.

Still another object of the present invention is to provide a coupling device that allows the wheel chair-/IV stand combination to travel up and down ramps without the wheels of the wheel chair or the IV stand leaving the floor.

SUMMARY OF THE INVENTION

The present invention comprises a coupling device and/or system for connecting a variety of transport devices to a wheeled IV stand. The present invention solves the aforementioned problems in the art and provides additional features heretofore unavailable in conventional devices and/or systems.

In one embodiment, the present invention is a system comprising a transport device having a plurality of wheels that come in contact with a first surface, a wheeled IV stand having a pole and a plurality of wheels that come in contact with a second surface, and a coupling device for connecting the wheeled IV stand to the transport device.

The coupling device comprises self adjusting means for maintaining the wheels of the wheeled IV stand and the wheels of the wheelchair in contact with the second surface and the first surface, respectively, when the first and second surfaces become uneven. The coupling device comprises a first arm and a support member. The first arm has a first end and a second end. The first end of the first arm is rotatably connected to the transport device while the second end of the first arm is connected to the support member. The support member in turn is connected to the wheeled IV stand.

The first end of the first arm comprises a clamp means attached thereto for releasably connecting the first arm to the transport device. The clamp means is preferably a quick action clamp.

The coupling device may further comprise a second arm. The second arm of the coupling device also has a first end and a second end. The first end of the second arm is connected to the transport device while the second end of the second arm is connected to the support member. Similar to the first arm, the second arm is rotatably connected to the support member. Also similar to the first arm, the first end of the second arm comprises a clamp means attached thereto for releasably connecting the second arm to the transport device. The clamp means of the second arm is likewise a quick action clamp.

In another embodiment of the present invention, the transport device may be a conventional wheel chair. Conventional wheel chairs typically have a first and second foot rest. In this embodiment, the first and second arms of the coupling device are attached to the corresponding first and second foot rests of the wheel chair.

In another embodiment of the present invention, the transport device may be a conventional geriatric chair. Geriatric chairs typically have only a single foot rest. In this embodiment, the first and second arms of the coupling device are both attached to the single foot rest.

In another embodiment of the present invention, the transport device may be a conventional stretcher. Stretchers typically have side bars. In this embodiment, the coupling device is raised to an appropriate height so that the first and second arms of the coupling device can be attached to the side bars.

The rotatable feature of the first and second arms of the coupling device is one significant feature of the present invention. By way of example, consider the wheel chair/coupling device/IV stand combination being pushed down a level hallway and approaching a downward sloping ramp. At the instance the wheel chair/coupling device/IV stand combination first starts to travel down the downward sloping ramp, the first and second arms of the coupling device begin to rotate downward thereby allowing the wheels of the IV stand to remain in contact with the floor which has changed from an even surface to a downward sloping surface. In other words, the rotatable feature of the first and second arms automatically "adjusts" for deviations in the plane of the floor. This feature is even more significant when the wheel chair/coupling device/IV stand combination is traveling down a ramp and then immediately up a ramp. C o n v en t i o n a l devices and/or systems employ a rigid interconnect means. A rigid connection between the wheel chair and the IV stand will not allow the wheels of the wheel chair and the wheels of the IV stand to remain in contact with the floor when abrupt changes in floor surface are encountered. In this situation the wheels of either the wheel chair or the IV stand are raised from the floor.

Another significant feature of the present invention is that the coupling device may attach to a conventional wheel chair and a conventional IV stand, or a conventional stretcher or geriatric chair. No modifications to the transport devices are necessary. Any necessary adjustments are made to the coupling device.

BRIEF DESCRIPTION OF THE DRAWINGS

The present invention as defined in the claims can be better understood with reference to the text and to the following drawings. The drawings are not necessarily to scale, emphasis instead being placed upon clearly illustrated principles of the present invention.

DETAILED DESCRIPTION OF THE PREFERRED EMBODIMENTS

Figure 1:
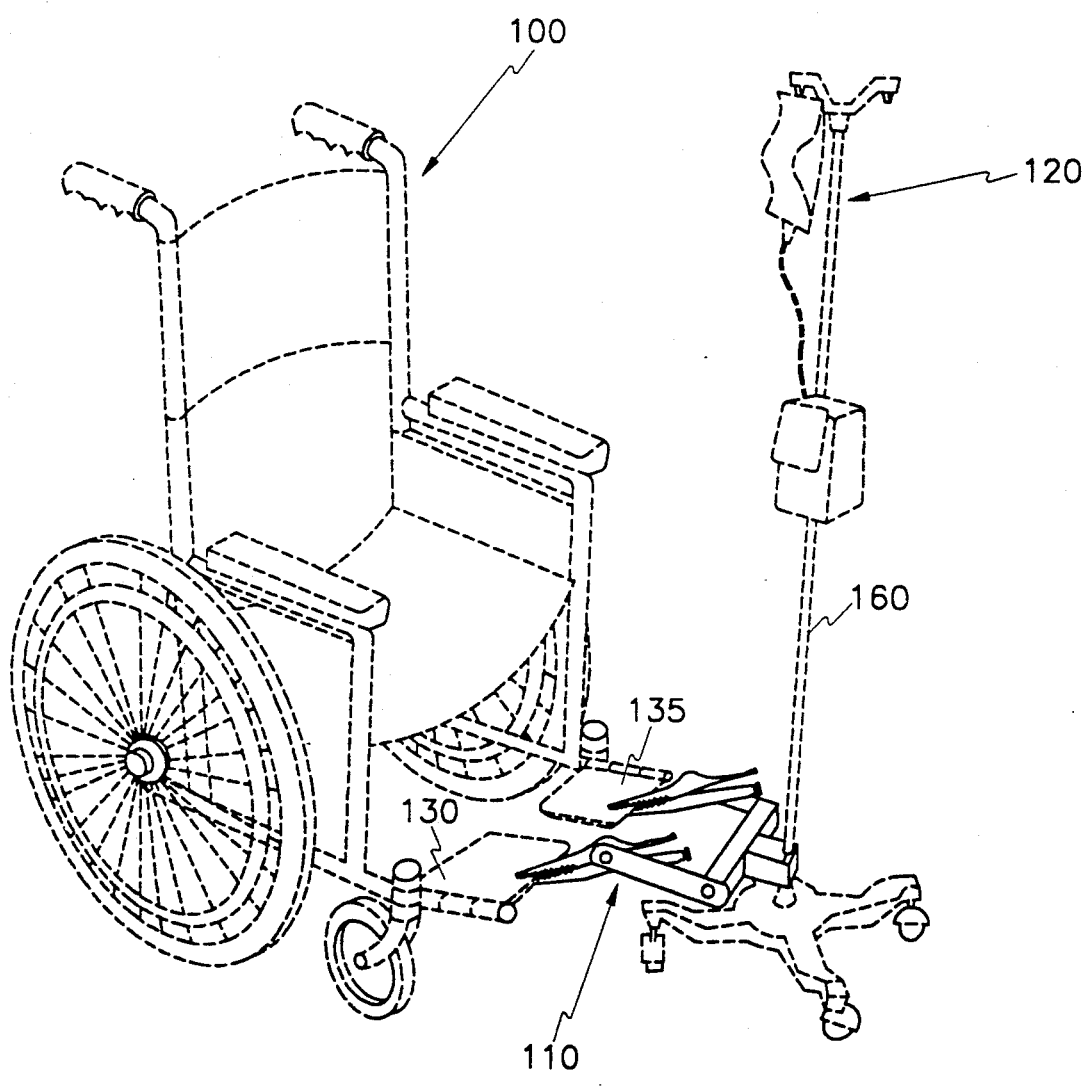
FIG. 1 illustrates a coupling device in a system for connecting a wheelchair to a wheeled IV stand.

Referring first to FIG. 1 wherein a coupling device 110 of the present invention is adapted to attach (or couple) a wheeled IV stand 120 to a wheel chair 100. In the embodiment shown by FIG. 1, and as will be more fully described herein, the coupling device 110 is adapted to attach to a first foot rest 130 and a second foot rest 135 of the wheel chair 100. The coupling device 110 is further adapted to attach to the pole 160 of the IV stand 120.

The wheel chair 100 and the IV stand 120 can be of conventional design that is found, for example, in most hospitals. In the embodiment shown by FIG. 1, no modifications to the wheel chair 100 or the IV stand 120 are necessary. The ability of the coupling device 110 to attach to a conventional wheel chair 100 and IV stand 120 is a significant feature of the present invention.

Figure 2:
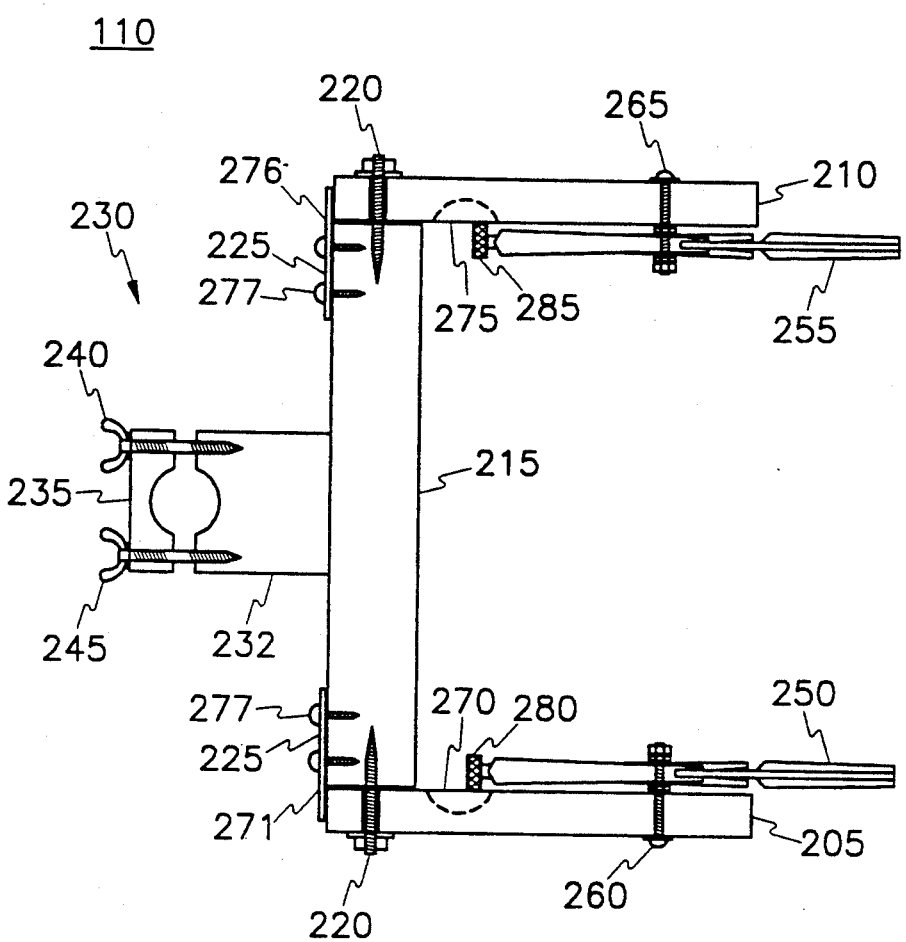
FIG. 2 shows a top view of the coupling device of FIG. 1.
Figure 3:
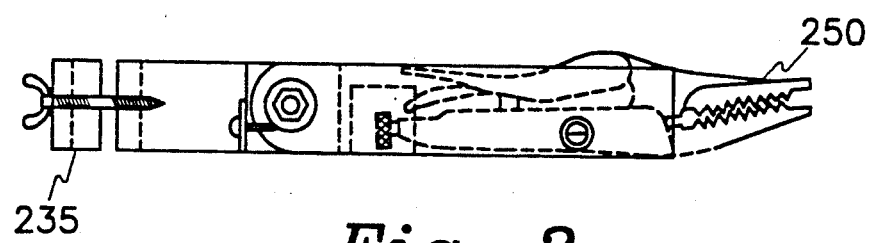
FIG. 3 shows a side view of the coupling device of FIG. 1.
Figure 4:
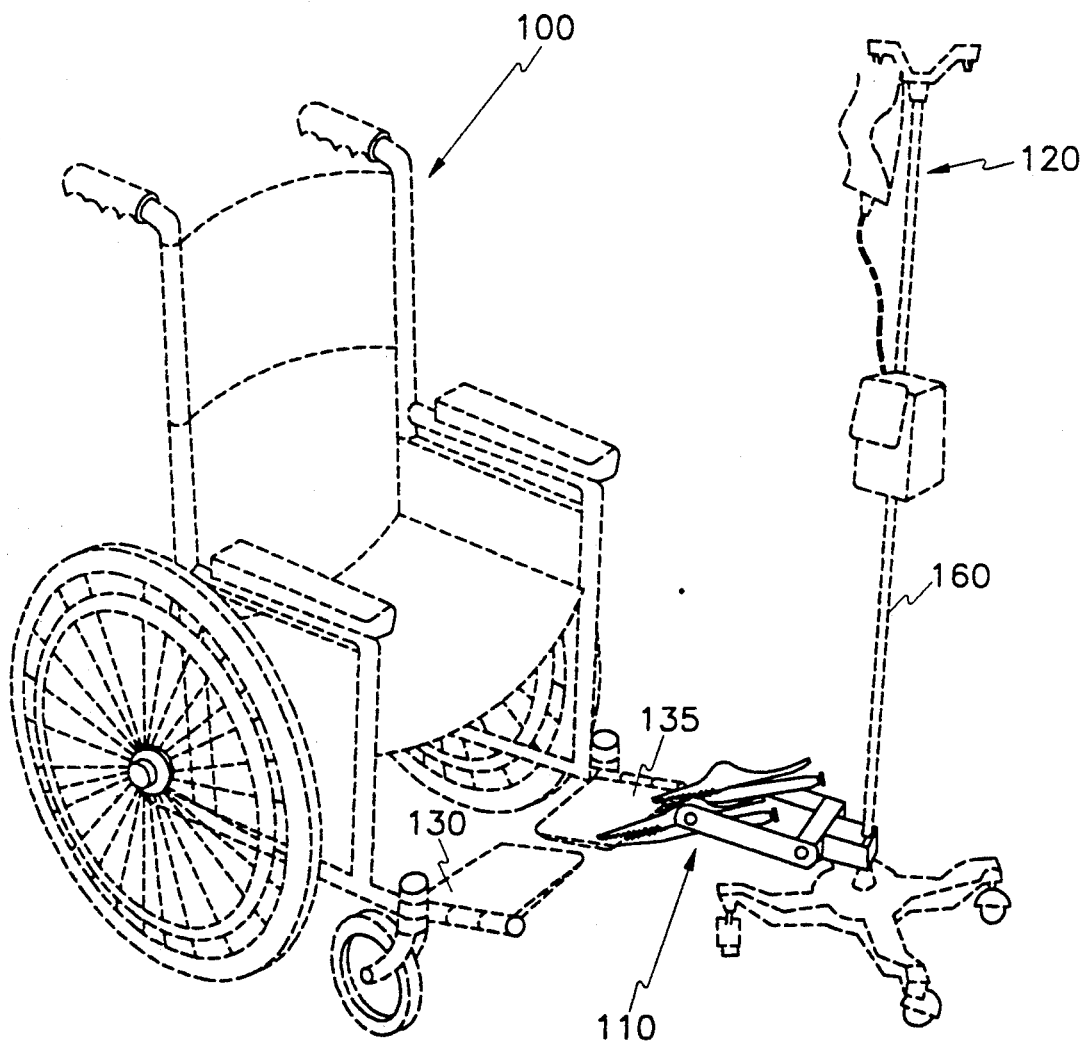
FIG. 4 illustrates the coupling device which is affixed to the wheelchair, in accordance with another aspect of the present invention.

Referring next to FIG. 2 wherein the coupling device 110 is shown in more detail. The coupling device 110 comprises a first arm 205 and a second arm 210 connected to a support member 215. In the preferred embodiment, the first arm 205 and the second arm 210 are each rotatably connected to the support member 215 using conventional screws (for example, shoulder bolts of an equivalent) 220. The rotatable feature of the first arm 205 and the second arms 215 allows the coupling device 110 to attach to the wheel chair 100 having foot rests 130 and 135 (shown in FIG. 1) which vary in height from the floor. As will be shown more fully herein, the rotatable feature also allows the wheels of the IV Stand 120 and the wheels of the wheelchair 100 to remain in contact with a floor which may become uneven (for example, when a ramp is encountered).

The coupling device 110 further comprises a first clamping means 250 and a second clamping means 255. First clamping means 250 and second clamping means 255 are connected to the first arm 205 and second arm 215, respectively. In the preferred embodiment, the first clamping means 250 and the second clamping means 255 are of a quick action type design. By way of example only, one type of quick action clamp is that of a conventional locking pliers sold under the trademark VICE-GRIP ® such as those readily available in most hardware stores. A quick action type design allows quick connect and disconnect of the clamping means 250 and 255 to the foot rests 130 and 135 of the wheel chair 100, (shown in FIG. 1). Further, use of a VICE-GRIP ® pliers is preferred because the clamping strength can be easily adjusted by the turning of a clamping knob 280 and 285. The clamping means 250 and 255 may be rotatably mounted to the first arm 210 and second arm 215 via conventional nut and bolt assembles 260 and 265, respectively. Like the rotatable feature of the first arm 210 and 215 relative to the support member 215, the rotatable feature of the clamping means 250 and 255 allows the coupling device 110 to attach to a wide variety of wheels chairs 100 (shown in FIG. 1) having foot rests 130 and 135 which may vary in height or direction relative to the floor.

Clamping means 250 and 255 can be of many conventional designs. It would preferred, however, that the clamping means 250 and 255 have the ability to quickly connect and disconnect. It would also be preferable for the clamping means 250 and 255 to have an adjustable feature so that foot rests 130 and 135 of variable thicknesses may be encountered.

The coupling device 110 further comprises a first recess 270 and a second recess 275. First recess 270 is formed in the first arm 205. The second recess 275 is formed in the second arm 210. The first recess 270 and the second recess 275 are provided so that the clamping knobs 280 and 285 may be easily turned.

The coupling device 110 further comprises an IV pole mounting means 230. In the preferred embodiment, the IV pole mounting means 230 comprises a first member 232 which can be an integral part of the support member 215 and a second member 235. First member 232 and second member 235 are adapted to receive the IV pole 160 (shown in FIG. 1) which is shown to have a circular shape. Screws 240 and 245 are provided to secure the IV pole 160 (shown in FIG. 1) within the first member 232 and second member 235.

It should be understood that IV pole mounting means 230 may take a variety of configurations other than that heretofore described. Such may be necessary so that a square shaped IV pole could be employed. By way of example only, such alternative designs may also be that of a hinged quick connect and disconnect means with a securing knob or lever. This alternative design would allow quick connect and disconnect of the IV stand 120 to the coupling device 110.

The coupling device 110 further comprises a first latch 270 and a second latch 275. Latches 270 and 275 provide a bearing surface for the arms 205 and 210 to rest on when arms 205 and 210 are rotated to a vertical position (for example, arms 205 and 210 may be in the vertical position when the coupling device 110 is in storage). Latches 270 and 275 are attached to the support member 215 using conventional screws 277.

The coupling device 110 of the present invention heretofore described may be designed in numerous ways. By way of example only, the coupling device 110 could have only the first arm 205 and not the second arm 215. Use of both the first arm 205 and the second arm 215 is preferred to ensure stability. However, it is contemplated that use of only one arm in the present invention would be satisfactory.

The coupling device 110 of the present invention has further been described with reference to coupling a conventional IV stand 120 to a conventional wheel chair 100. The coupling device 100, however, can be used to couple many other types of transport devices to a wheeled IV stand. By way of example only, the coupling device 110 could be used to couple a stretcher to the wheeled IV stand 120 (shown in FIG. 1). In this embodiment, the coupling device 110 would be raised (elevated) to the upper end of the IV pole 160 of the IV stand 120 so that the arms 205 and 25 could connect to the side bars of the stretcher.

Alternatively, the coupling device 110 could be used to couple a geriatric chair to the IV stand 120. In this embodiment, the first and second clamping means of the coupling device would each connect to the single foot rest (most geriatric chairs have only a single foot rest as compared with conventional wheel chairs which have two separate foot rests).

The foregoing description is intended primary for purposes of illustration. The coupling device 110 of the present invention may be embodied in other forms or carried out in other ways without departing from the spirit or scope of the invention. Modifications and variations still falling within the spirit or the scope of the invention will be readily apparent to those of ordinary skill in the art.

What is claimed:
1. A system comprising:
   a wheelchair having first and second footrests and a plurality of wheels in contact with a first surface;
   a wheeled IV stand having a pole and plurality of wheels in contact with a second surface;
   a coupling means for connecting said wheeled IV stand to said wheelchair, for confining relative movement of said wheeled IV stand and said wheelchair within a fixed, substantially vertical, geometric plane, and for maintaining said wheels of said wheelchair in contact with said first surface and said wheels of said wheeled IV stand in contact with said second surface when said first surface and said second surface become uneven, comprising;
   a first arm and a second arm rotatably connecting a support member to said first and second footrests, respectively;
   means for connecting said support member to said IV stand; and
   a locking plier for releasably connecting each of said first and second arms to said footrests, respectively.
2. A system comprising:
   a wheelchair having at least one footrest and a plurality of wheels in contact with a first surface;
   a wheeled IV stand having a pole and plurality of wheels in contact with a second surface;
   a coupling means for connecting said wheeled IV stand to said wheelchair, for confining relative movement of said wheeled IV stand and said wheelchair within a fixed, substantially vertical, geometric plane, and for maintaining said wheels of said wheelchair in contact with said first surface and said wheels of said wheeled IV stand in contact with said second surface when said first surface and said second surface become uneven, comprising;
   a first arm and a second arm rotatably connecting a support member to said at least one footrest;
   means for connecting said support member to said IV stand; and
   at least one locking plier for releasably connecting each of said first and second arms to said at least one footrest.

* * * * *

UNITED STATES PATENT AND TRADEMARK OFFICE
CERTIFICATE OF CORRECTION

PATENT NO. : 5,172,927
DATED : December 22, 1992
INVENTOR(S) : James R. Bobb, et al.

It is certified that error appears in the above-indentified patent and that said Letters Patent is hereby corrected as shown below:

On the title page, item (54) title, delete "TV" and insert --IV--.

Signed and Sealed this

Twenty-first Day of December, 1993

Attest:

BRUCE LEHMAN

Attesting Officer    Commissioner of Patents and Trademarks